United States Patent [19]

Welsh

[11] 4,384,853
[45] * May 24, 1983

[54] EJECTOR HOLDER FOR CAPSULE-LIKE CARTRIDGE

[75] Inventor: Richard E. Welsh, Milford, Del.

[73] Assignee: Dentsply Research & Development Corp., Milford, Del.

[*] Notice: The portion of the term of this patent subsequent to May 18, 1999, has been disclaimed.

[21] Appl. No.: 344,254

[22] Filed: Jan. 29, 1982

Related U.S. Application Data

[63] Continuation-in-part of Ser. No. 252,558, Apr. 9, 1981, Pat. No. 4,330,280.

[51] Int. Cl.³ .............................................. A61C 5/04
[52] U.S. Cl. ...................................... 433/90; 222/326
[58] Field of Search .............................. 433/90, 89, 80

[56] References Cited
U.S. PATENT DOCUMENTS 4,330,280  5/1982  Dougherty et al. ................... 433/90

*Primary Examiner*—Robert Peshock
*Attorney, Agent, or Firm*—C. Hercus Just

[57] ABSTRACT

A manually operable ejector holder for effecting discharge of a capsule-like cartridge of cylindrical shape open at one end to receive a measured charge of material and provided with an annular flange at the open end, the other end being closed but provided with an angular discharge nipple and the holder having a cylindrical body provided with an ejecting plunger operated by a handle and a cooperative pivoted lever member. The forward end of the cylindrical body is partially cutaway in a radial direction for a limited distance longitudinally to provide a hollow seat to receive the flanged end of the cartridge and the seat having an undercut groove to receive the flange of said cartridge, and the sidewalls of the seat at the upper edges having limited flexibility and spaced apart a slightly less distance than the diameter of the cartridge body to effect a limited snap-acting connection of the cartridge to the holder. Several embodiments of lever members and support mechanism therefor are provided.

10 Claims, 10 Drawing Figures

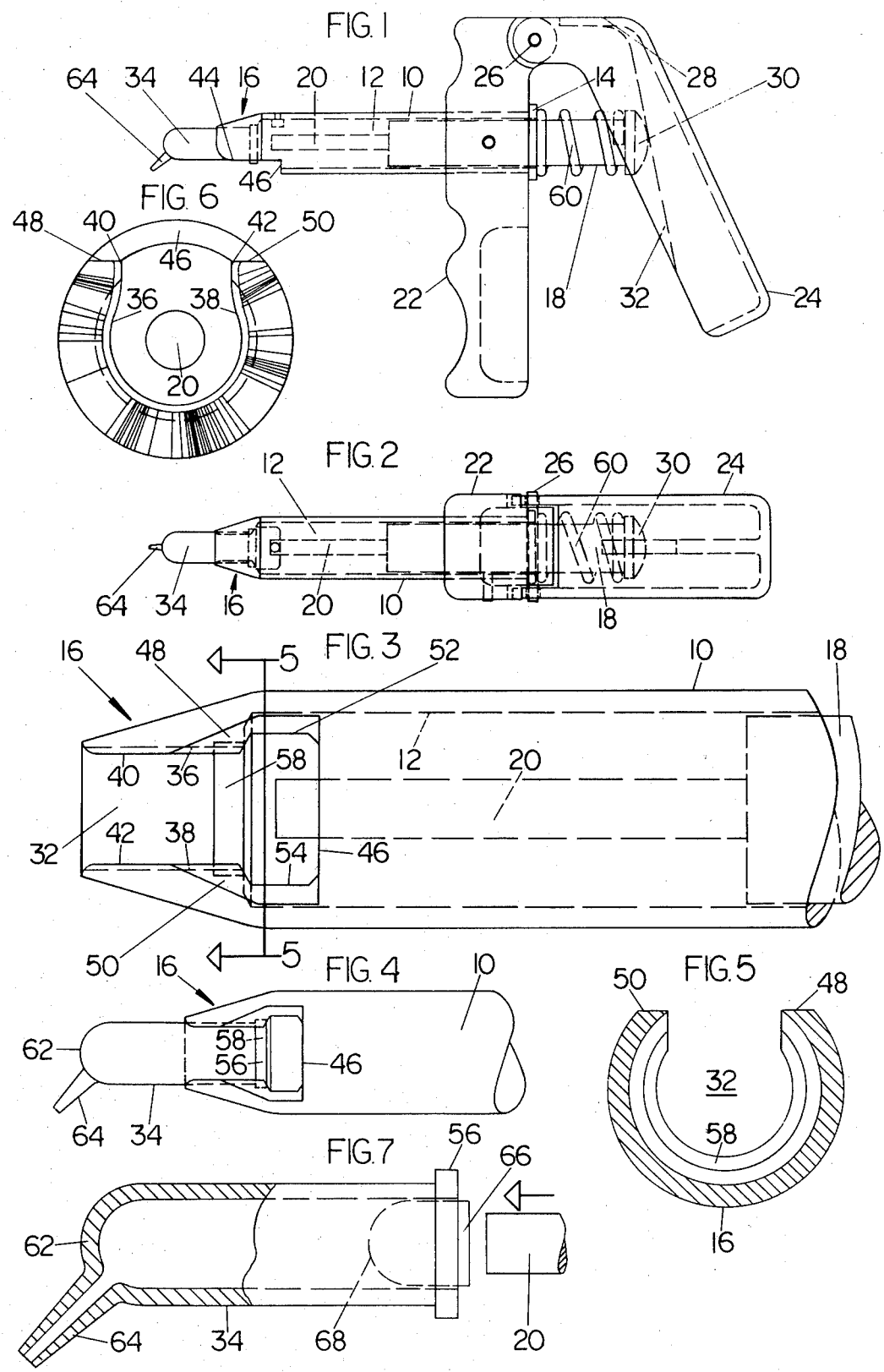

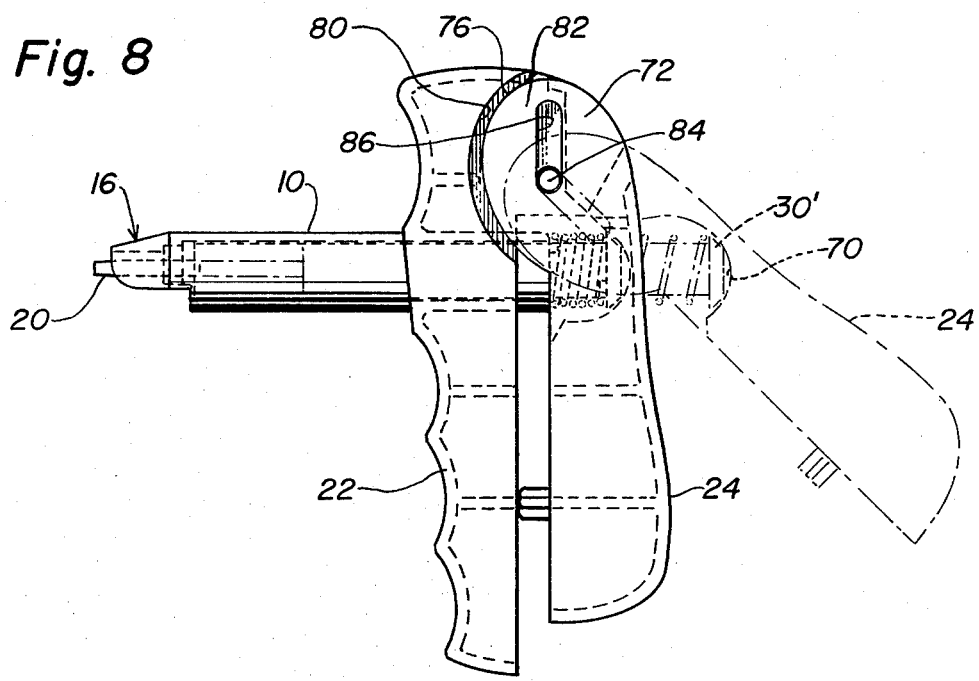
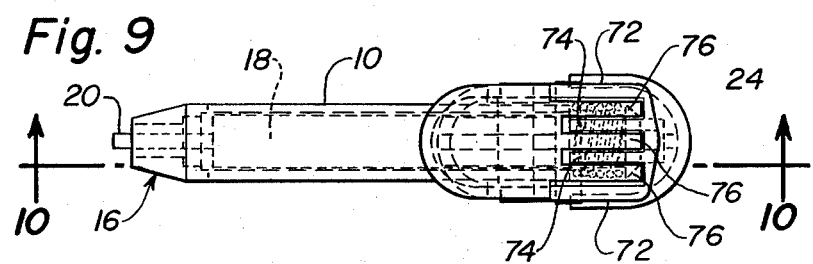
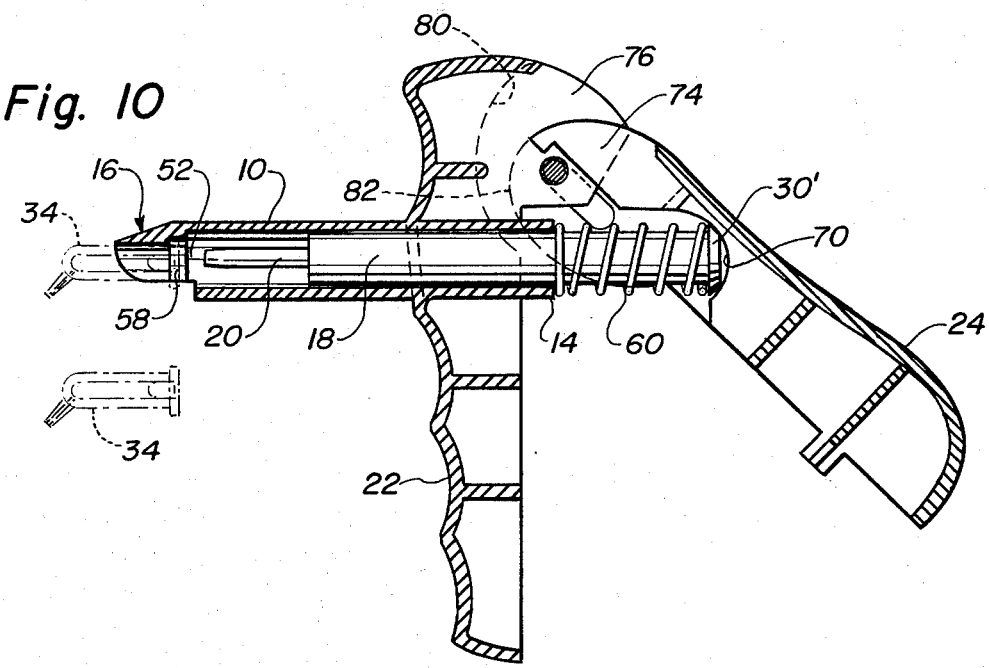

EJECTOR HOLDER FOR CAPSULE-LIKE CARTRIDGE

REFERENCE TO RELATED APPLICATION

This application is a Continuation-in-Part of Application Ser. No. 252,558, filed Apr. 9, 1981 now U.S. Pat. No. 4,330,280 issued May 18, 1982, and entitled "EJECTOR HOLDER FOR CAPSULE-LIKE CARTRIDGES".

BACKGROUND OF THE INVENTION

In recent years it has become popular to package various types of material, especially medicinal or quasi-medicinal types in sealed cartridges, insertable in a suitable type of holder and/or ejector device, for purposes of preserving purity of the medicament and the like, insuring a patient of accurately measured quantities, as well as minimizing effort now required in introducing bulk amounts of material into syringes and ejecting measured quantities thereof, for example. Various previous efforts in this direction are illustrated and described in various prior U.S. patents, particularly U.S. Pat. No. 3,581,399 to Dragan, dated June 1, 1971, in which a typical example of loaded cartridge is illustrated in conjunction with one type of holder and discharge device.

Other efforts have been made to produce similar devices, one of these comprising the subject matter of prior U.S. Pat. No. 3,900,954, also to Dragan, dated Aug. 26, 1975, and comprising a simpler version than in Dragan's U.S. Pat. No. 3,581,399. Also, another U.S. Pat. No. to Dragan, 4,198,756, dated Apr. 22, 1980, shows an ejector design for the aforementioned cartridges.

It has been found in the operation of the Dragan devices, particularly relative to the curved discharge end of the capsule or cartridges that there have been occasions when the leading end of the ejecting plunger or the piston within the cartridge pushed through the wall adjacent the outer end of the cartridge. Particularly for purposes of obviating this difficulty and also for providing what is believed to be a simple and improved compartment at the forward end of the barrel of the holder, as well as also providing an improved cartridge not subject to the difficulties of Dragan's cartridges, which is free of difficulties similar to those described with respect to the Dragan cartridge, the present invention has been devised and details thereof are set forth hereinbelow.

The present invention also comprises a simplified improvement over U.S. Pat. No. 4,295,828 in the name of Helmut Rudler, dated Oct. 20, 1981, and entitled "Ejector Holder for Syringe-type Cartridge", the invention covered thereby being assigned to the same assignee as the invention of the instant application.

SUMMARY OF THE INVENTION

It is among the principal objects of the present invention to provide preferably a one-piece barrel having integral and relatively simple means at the forward end thereof to seat and retain an improved cartridge having an annular flange at the end opposite the discharge end, said cartridge being retained by a simple snap-acting arrangement.

It is another object of the invention to provide at the forward end of said barrel a compartment in which said aforementioned seat for the flange of the cartridge is included, said compartment being formed simply by cutting away part of the wall comprising the forward end of the barrel a limited distance inwardly and axially from the outer end of the barrel, the surface formed by the cutaway arrangement lying within a plane parallel to the axis and radially spaced from the same a short distance, the inner end portion of the cutaway arrangement being wider than the portion extending forwardly therefrom for purposes of receiving the flange of the cartridge in a seat for said flange which is forwardly of the inner end of the compartment and into which the flange is inserted to mount the cartridge in the compartment.

A further object of the invention is to provide in the compartment a semi-cylindrical surface from which opposite, substantially parallel sidewalls extend and the upper edges of said sidewalls extending a very limited distance toward each other and said sidewalls having limited flexibility to provide the snap-acting retaining arrangement referred to above.

Still another object of the invention is to provide on the rearward end of the barrel a handle fixed thereto and extending transversely thereto, preferably in opposite directions from the axis of the barrel, a plunger being reciprocably mounted in the barrel for engagement at one end with a combination closure plug and piston in a cartridge, when mounted in the forward end of the barrel, and several embodiments of an actuating lever are provided which respectively are a lever of the second class and are pivotally associated with one end of said handle and extend from the pivot means thereof past the opposite end of the plunger and engaging the same for reciprocation thereof, as aforesaid, when the lever is manually activated toward the handle, spring means being provided on the plunger to retract the same from engagement of the forward end thereof with a cartridge.

Another object closely ancillary to the foregoing object is to provide one embodiment of lever which has a fixed pivot axis relative to one end of the handle, whereby the mid-portion of the lever has a sliding engagement with the aforementioned opposite end of the plunger, while another embodiment of lever has a slidable pivot fulcrum relationship with the associated end of the handle and said opposite end of the plunger has a rocking engagement with an intermediate portion of the lever.

Still another object of the invention, also ancillary to the several foregoing objects, and especially the latter embodiment of lever which has a rocking engagement with the opposite end of the plunger, is to provide an engagement between said opposite end of the plunger and intermediate portion of said lever which is in the nature of a partial ball and socket configuration, whereby the lever pivotally moves about the center of the partial ball-like member, while the slidable pivot fulcrum end of the handle moves relative to the pivot axis thereof.

Details of the foregoing objects and of the invention, as well as other objects thereof, are set forth in the following specification and illustrated in the accompanying drawing comprising a part thereof.

BRIEF DESCRIPTION OF THE DRAWING

FIG. 1 is a side elevation of an ejector holder supporting a capsule-like cartridge in accordance with the principles of the present invention.

FIG. 2 is a top plan view of the holder and cartridge shown in FIG. 1.

FIG. 3 is a fragmentary enlarged bottom plan view of the forward end of the barrel of the ejector holder shown in FIGS. 1 and 2.

FIG. 4 is a fragmentary bottom plan view of the ejector holder similar to FIG. 3, but on a smaller scale, and illustrating a cartridge supported in the forward end of the barrel.

FIG. 5 is a vertical sectional view of the forward end portion of the barrel of the ejector holder shown in FIG. 3, as seen on the line 5—5 thereof.

FIG. 6 is a front end view of the forward end of the barrel shown in FIGS. 1–4.

FIG. 7 is a side elevation, partly broken away, of a cartridge similar to that shown in FIGS. 1, 2 and 4, but on a larger scale, and illustrating a piston inserted in the open end of the cartridge and also showing fragmentarily a portion of a plunger rod of the ejector holder adapted to engage said piston.

FIG. 8 is a side elevation of another embodiment of ejector.

FIG. 9 is a top plan view of FIG. 8.

FIG. 10 is a vertical section of FIG. 9 as seen on line 10—10 thereof.

DETAILED DESCRIPTION OF THE PREFERRED EMBODIMENT

Referring to FIG. 1, there is shown therein an ejector holder which includes the principles of one embodiment of the present invention and comprising a barrel 10 having an interior bore 12 extending from the rearward end 14 of the barrel toward the forward end 16 thereof for purposes of receiving a plunger 18 of the same diameter as that of the interior bore 12 for the major portion of the length of the plunger, the forward end of the plunger having a smaller diameter extension 20.

The rearward end 14 of the barrel 10 extends through and is fixed to a handle member 22 with which the barrel 10 is perpendicular. Pivotally connected to the handle 22 is an operating lever 24, the upper end of which is pivotally connected to the upper end of handle 22 by a pivot pin 26 which is fixed relative to the upper end of handle member 22. The upper end 28 of operating lever 24 is offset laterally to facilitate operation of the lever 24 with respect to the outer end of plunger 18 which terminates in a button 30, which is slidably engaged by a portion of the inner surface 32 of operating lever 24.

From FIGS. 1–4, it will be seen that the forward end 16 of the barrel 10 is tapered and is provided with a longitudinally extending opening comprising compartment 32 which extends rearwardly from the terminal end of the forward end 16 toward the interior bore 12. The lower surface of compartment 32, as viewed in FIG. 3, is semi-cylindrical and is complementary to the elongated body of cartridge 34 so as to receive and seat the same, as shown in FIGS. 1, 2 and 4. Cartridge 34, per se, is the subject matter of a companion division-in-part application filed on even date herewith. The sidewalls 36 and 38 of compartment 32 extend upwardly from the semi-cylindrical bottom surface shown in FIG. 3 and are parallel to each other for a limited distance and the upper edges 40 and 42 extend toward each other a limited distance. Said uppermost portions of sidewalls 36 and 38 also have limited flexibility, whereby the distance between the upper edges 40 and 42 of said sidewalls preferably is slightly less than the diameter of the cartridge 34, whereby there is a snap-acting retaining function provided by said sidewalls and the upper edges 40 and 42 with respect to the cartridge 34 when the latter is inserted in the compartment 32.

The forward end 16 of the barrel 10 also has a cutaway portion 44 extending longitudinally rearward to form a shoulder 46, which determines the inner end of the cutaway portion. Due to the fact that the forward end 16 is tapered and the barrel 10 otherwise is circular, said cutaway arrangement provides flat surfaces 48 and 50. Also, as best shown in FIG. 3, the sidewalls of the compartment 32, at the inner ends thereof, have lateral recesses 52 and 54 which are spaced apart a greater distance than the diameter of the annular exterior flange 56 in order to permit the insertion of the flange into compartment 32 which, following radial insertion movement thereof into the compartment, the cartridge may be moved axially forward for disposition of the flange 56 in an undercut seat 58, which is clearly shown in FIGS. 3–5. Said seat, in conjunction with the portion of the compartment 32 extending forwardly therefrom, provides a firm means for supporting a cartridge 34, which is retained seated in said compartment, especially by means of the snap-fitting arrangement provided by the upper edges 40 and 42 of the sidewalls 36 and 38, as described hereinabove. However, even if the snap-fitting feature is omitted, the seat 58 will assure firm connection of the cartridge with the barrel in use.

Without restriction thereto, the preferred material from which the barrel 10, handle member 22 and operating lever 24 are formed, is a suitable rigid plastic material in order that these elements may be formed readily and accurately by molding from raw plastic material; obviously, the coiled spring 60 is formed from spring wire for purposes of retracting the plunger 18 when the operating lever 24 is released, following an ejection of material from the cartridge 34. Similarly, the cartridge 34 also is formed by molding from appropriate, preferably rigid, synthetic resin or plastic material by means of a suitable mold. The intermediate body portion of the capsule 34 is of uniform interior and exterior diameter and extends from the flange 56 adjacent the open end of the cartridge to the opposite closed end 62. The body portion is cylindrical, whereas the closed end 62 is hemispherical but is provided with an angularly extending discharge nipple 64, the opening of which is preferably a very fine dimension of small diameter. To effect ejection of material from the cartridge 34, such as dental filling material, cement, or other viscous dental material and the like, for example, the cartridge 34 includes a piston 66, which is closely complementary in diameter to the interior of the cartridge 34, and the inner end 68 thereof also is hemispherical and complementary to the interior of the closed end 62 of the cartridge. The outer end of the piston may be flat for engagement, for example, with the extension 20, shown fragmentarily in FIG. 7, when the plunger 18 is moved forwardly by actuation of the operating lever 24.

Removal of the capsule 34 from the compartment 32 is accomplished readily by snapping the cartridge outwardly beyond the somewhat flexible upper edges 40 and 42 of the compartment after the contents within the cartridge have been discharged or exhausted, as required.

Another embodiment of ejector from that shown in FIGS. 1–7 is illustrated in FIGS. 8–10, both embodiments utilizing the cartridge-attaching means shown at the forward or left-hand end of the barrel 10 as illustrated in FIGS. 8–10 in the second embodiment and, correspondingly, in FIGS. 1–7 of the first embodiment. In FIGS. 8–10, it will be seen that the handle 24 is fixedly connected to the rearward end of the barrel 10 in the same manner as the corresponding element in FIGS. 1–7. However, the operating lever 24 is connected to the handle member 22 in a different manner from that illustrated in FIGS. 1–7, details of which are as follows:

The plunger 18 is reciprocable in the barrel 10 in opposite direction for purposes of moving the extension 20 at the forward end thereof toward the cartridge 34 for purposes of effecting discharge thereof. The rearward or right-hand end of the plunger 18, as viewed in FIGS. 8 and 10, is provided with a button 30' which is slightly different from the button 30 shown in FIGS. 1–7, in that the same actually constitutes a part of a ball and socket connection, of which the button 30' is a fragmentary ball or at least functions as a fragmentary ball, the perimeter of which has a greater diameter than that of the plunger 18 in order that the compression spring 60 may be disposed with its opposite ends respectively between the button 30' and the rearward end 14 of the barrel 10. The other part of the fragmentary ball and socket joint or connection comprises a somewhat hemi-spherical seat 70 formed in the inner portion of the lever 24 intermediately of the ends thereof, whereby the modified button 30' actually comprises a fulcrum about which the seat 70 rotates within the same plane as the handle 22 and lever 24, the center of rotation being coincident with the axis of the plunger 18.

It has been found that movement of the lever 24 toward and from the handle 22 is facilitated by the more-or-less fragmentary ball and socket joint or connection comprising the button 30' and seat 70 when engaging the handle and lever somewhat in pistol-gripping manner by one hand of an operator, especially when moving the lever 24 from the extended position shown in FIG. 10 to the fully closed position shown in FIG. 8, the initial position also being shown in FIG. 8 in phantom.

In order to permit the operation of the lever 24 in the manner just described, however, the upper ends of both the handle 22 and lever 24 are modified from the arrangement shown in the embodiment of FIGS. 1–7, in the following respects:

Especially as shown in FIG. 9, it will be seen that the upper end of lever 24 is provided with a plurality of similar parallel leaves 72 and 74, the leaves 72 being outermost and the leaves 74 being disposed inwardly thereof. Interdigitated with the leaves 72 and 74 of lever 24 are a plurality of three similar leaves 76 on the upper end of handle 72. Further, the exterior side 78 of the upper end of handle 22 respectively is provided with relatively shallow and flat arcuate sockets 80, see FIG. 8, to accommodate the corresponding arcuate configurations 82 of lever 24.

In view of the pivotal movement of lever 24 about the axis of the modified button 30' and the plunger 18, it will be seen that the upper end of lever 24, which actually is a lever of the second class, is provided with a floating fulcrum in the form of a pin 84 which extends transversely through the leaves 76 of handle 22, and each of the leaves 72 and 74 of the lever 24 are provided with slots 86 which are all parallel to each other and commonly receive the pin 84 and thereby provide the aforementioned floating fulcrum for the lever 24 and easier hand operation thereof.

From the foregoing, it will be seen that the several embodiments of ejector holders and the particular type of cartridge to be used therewith are of very simple, but highly effective design, to permit sure and quick mounting of the cartridge within the compartment in the forward end of the barrel of the holder and, with equal facility, removal of the cartridge therefrom is readily achieved. Assembly of all of the components, particularly when manufactured by molding of suitable plastic or synthetic resin assures accurate dimensions and the design of all the components is such that they are readily capable of being formed by molding from plastic material.

Not only is the cartridge capable of serving as a receptacle for material to be discharged when filled, for example, from a storage amount, but, even more importantly, the cartridge can be filled at a factory with predetermined quantities of material and sealed therein by application of the piston 66, which, under the circumstances, serves as a closure for the cartridge. Further, during filling, air in the cartridge in advance of the material can be discharged through the nipple 64 until filled and then the open end of the nipple may suitably and inexpensively be closed by suitable seal means, such as a small piece of sheet material having pressure-sensitive cement on one side and fold said piece across the nipple in any suitable manner.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A manually operable ejector holder for a capsule-like cartridge loaded with viscous material and the like and having an annular collar on one end and a discharge tip on the other, said holder comprising in combination, an elongated barrel having forward and rearward ends, a plunger reciprocable therein and one end thereof projecting beyond said rearward end of said barrel, a handle connected to said rearward end of said barrel and extending substantially transversely to the axis thereof, a lever manually operable relative to said handle and barrel to reciprocate said plunger relative to the other end of said barrel for engagement with a capsule when disposed therein, and said other end of the barrel being cutaway longitudinally a limited distance to provide a compartment having sidewalls extending a limited distance beyond the axis of said barrel, an undercut groove formed in said compartment within said sidewalls to receive the annual collar on a cartridge to prevent relative axial movement between said cartridge and compartment, and the outer portions of the sidewalls of said compartment having limited flexibility and extending toward each other a slightly lesser distance than the diameter of said compartment to effect a snap-acting retaining means for the body of a cartridge when inserted into said compartment.

2. The ejector holder according to claim 1 in which the sidewalls of said compartment at the inner end thereof are recessed laterally a greater distance than the diameter of an annular flange on a cartridge to permit the flange thereon to be inserted into said compartment incident to being positioned into said undercut groove, and said undercut groove at the upper ends thereof having opposite wall portions in said compartment extending toward each other a limited distance less than the diameter of an annular cartridge flange to provide a seat for said flange forward of the portion of said laterally recessed portion of said sidewalls of said compartment and from which said flange cannot be removed laterally.

3. The ejector holder according to claim 1 in which the sidewalls of said compartment forwardly of said undercut groove extend outwardly in a radial direction from a semi-cylindrical innermost surface of uniform diameter and the distance between said sidewalls being uniform throughout the length thereof forwardly of said undercut groove.

4. The ejector holder according to claim 1 in which said handle extends transversely in opposite directions relative to the axis of said barrel, and said lever means being connected to one end of said handle by pivotal means and extending from said pivotal means past said projecting end of said plunger, and said lever means having an arcuate surface intermediately of the ends thereof engaging said projecting end of said plunger, said arcuate surface having a center of curvature coincident with the axis of said plunger for pivotal movement of said lever relative thereto when said lever is moved toward said handle to move said plunger toward the forward end of said barrel.

5. A manually operable extruder for extruding viscous dental material and the like from cartridges and comprising in combination:
 (a) a tubular barrel having a forward end arranged to support a capsule containing said material and having discharge means on one end thereof,
 (b) a handle member connected to the opposite end of said barrel and extending substantially transversely thereto,
 (c) a plunger reciprocable within said barrel and having one end adapted to be projected toward the forward end of said barrel and the opposite end extending beyond said opposite end of said barrel,
 (d) a lever of the second class mounted adjacent to said handle and intermediately of the ends thereof having means engagable with said opposite end of the plunger in pivotal rocking movement about the axis of said plunger when said lever is moved manually toward said handle, and
 (e) pivotal means between similar adjacent ends of said handle and lever comprising interengaged pivot and slot means thereon operable to permit said pivotal rocking movement of said lever relative to said opposite end of said plunger.

6. The ejector holder according to claim 5 wherein said lever and opposite end of said plunger have interengaging partial ball and socket means to effect said pivotal rocking movement therebetween, whereby manual engagement of said lever and handle to move the same toward each other permits a squeezing action substantially devoid of any sliding tendency in such manual contact with said lever.

7. The ejector holder according to claim 6 wherein said pivotal means on the ends of said lever and handle comprise a transverse pivot member fixed to one of the same and slots receiving said pivot member being formed in the other substantially longitudinally thereof.

8. The ejector holder according to claim 6 in which the partial ball is on said opposite end of the plunger and coaxial therewith, and the partial socket is formed in said lever in a surface nearest said handle.

9. The ejector holder according to claim 8 in which the partial ball on said plunger has a circumference of greater diameter than the diameter of said plunger, and a coiled spring surrounds a portion of said plunger adjacent to said partial ball, the opposite ends of said spring respectively engaging said opposite end of the barrel and said partial ball.

10. The ejector holder according to claim 7 further characterized by said transverse pivot being fixed to said handle and said slots being formed in the adjacent end of said lever, whereby said lever is slidably pivotal relative to said handle.

* * * * *

REEXAMINATION CERTIFICATE (2124th)
United States Patent [19]
Welsh

[11] B1 4,384,853

[45] Certificate Issued Nov. 9, 1993

[54] EJECTOR HOLDER FOR CAPSULE-LIKE CARTRIDGE

[75] Inventor: Richard E. Welsh, Milford, Del.

[73] Assignee: Dentsply Research & Development Corp., Milford, Del.

Reexamination Request:
No. 90/002,815, Aug. 14, 1992

Reexamination Certificate for:
Patent No.: 4,384,853
Issued: May 24, 1983
Appl. No.: 344,254
Filed: Jan. 29, 1982

[51] Int. Cl.⁵ ............................................. A61C 5/04
[52] U.S. Cl. ........................................ 433/90; 222/326
[58] Field of Search ........................... 433/90, 89, 80; 222/260, 326, 391, 472; 604/61

[56] References Cited
U.S. PATENT DOCUMENTS

| | | | |
|---|---|---|---|
| 1,926,496 | 9/1933 | Parker | 221/423 |
| 1,972,161 | 9/1934 | Parker | 221/423 |
| 3,076,455 | 2/1963 | McConnaughey | 128/218 |
| 3,341,085 | 9/1967 | Sundholm | 222/260 |
| 4,198,756 | 4/1980 | Dragan | 433/90 |

*Primary Examiner*—Cary E. O'Connor

[57] ABSTRACT

A manually operable ejector holder for effecting discharge of a capsule-like cartridge of cylindrical shape open at one end to receive a measured charge of material and provided with an annular flange at the open end, the other end being closed but provided with an angular discharge nipple and the holder having a cylindrical body provided with an ejecting plunger operated by a handle and a cooperative pivoted lever member. The forward end of the cylindrical body is partially cutaway in a radial direction for a limited distance longitudinally to provide a hollow seat to receive the flanged end of the cartridge and the seat having an undercut groove to receive the flange of said cartridge, and the sidewalls of the seat at the upper edges having limited flexibility and spaced apart a slightly less distance than the diameter of the cartridge body to effect a limited snap-acting connection of the cartridge to the holder. Several embodiments of lever members and support mechanism therefor are provided.

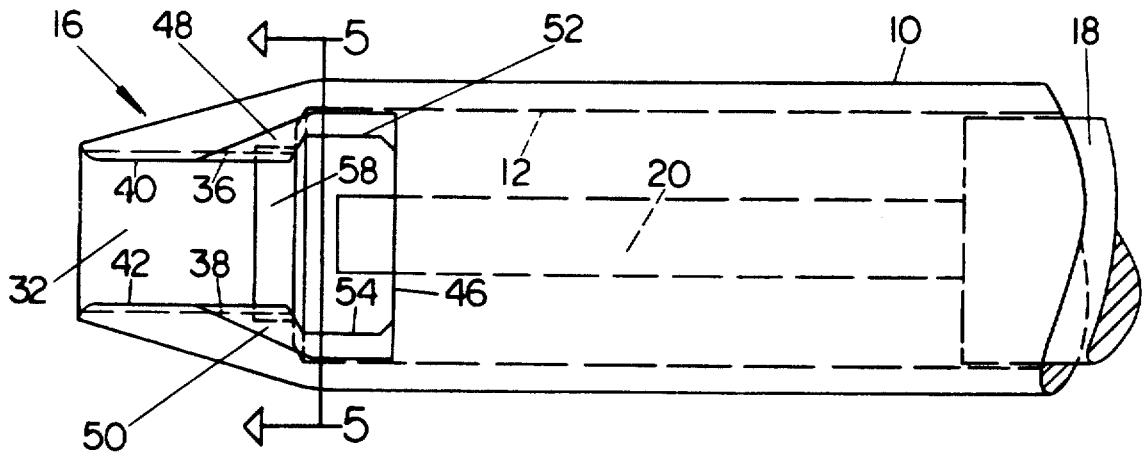

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 7 is cancelled.

Claims 1, 5, and 10 are determined to be patentable as amended.

Claims 2-4, 6, 8 and 9 dependent on an amended claim are determined to be patentable.

1. A manually operable ejector holder for a capsule-like cartridge loaded with viscous material and the like and having an annular collar on one [and] *end,* a discharge tip on the other *end, and an intermediate body portion in between,* said holder comprising in combination, an elongated barrel having forward and rearward ends *and also having an interior bore,* a plunger reciprocal therein and one end thereof projecting beyond said rearward end of said barrel, a handle connected to said rearward end of said barrel and extending substantially transversely to the axis thereof, a lever manually operable relative to said handle and barrel to reciprocate said plunger relative to the other end of said barrel for engagement with a capsule when disposed therein, and said other end of the barrel being cutaway longitudinally a limited distance to provide a compartment having sidewalls extending a limited distance beyond the axis of said barrel, an undercut groove formed *forward of said interior bore and rearwardly* in said compartment within said sidewalls to receive the [annual] *annular* collar on a cartridge to prevent relative axial movement between said cartridge and compartment, and the outer *longitudinally-extending* portions of the sidewalls of said compartment having limited flexibility and extending toward each other a slightly lesser distance than the diameter of said [compartment] *cartridge intermediate body portion* to effect a snap-acting retaining means for the body of a cartridge when inserted into said compartment, *said retaining means extending longitudinally a distance forward of said undercut groove substantially greater than the longitudinal length of said annular collar to hold a substantial portion of said cartridge intermediate body portion.*

5. A manually operable extruder for extruding viscous dental material and the like from cartridges and comprising in combination:
   (a) a tubular barrel having a forward end arranged to support a capsule containing said material and having discharge means on one end thereof,
   (b) a handle member connected to the opposite end of said barrel and extending substantially transversely thereto,
   (c) a plunger reciprocable within said barrel and having one end adapted to be projected toward the forward end of said barrel and the opposite end extending beyond said opposite end of said barrel,
   (d) a lever of the second class mounted adjacent to said handle and intermediately of the ends thereof having means engagable with said opposite end of the plunger in pivotal rocking movement about the axis of said plunger when said lever is moved manually toward said handle, and
   (e) [pivotal means] *a floating fulcrum* between similar adjacent ends of said handle and lever comprising [interengaged pivot and slot means thereon operable to permit said pivotal rocking movement of said lever relative to said opposite end of said plunger] *a transverse pivot member fixed to one of said handle and lever and at least one slot being formed substantially longitudinally in the other of said handle and lever for receiving said pivot member.*

10. The ejector holder according to claim [7] *5* further characterized by said transverse pivot *member* being fixed to said handle and said [slots] *at least one slot* being formed in the adjacent end of said lever, whereby said lever is slidably pivotal relative to said handle.

* * * * *